(12) United States Patent
Ertugrul et al.

(10) Patent No.: US 10,736,712 B2
(45) Date of Patent: Aug. 11, 2020

(54) CLAMPING DEVICE FOR CLAMPING A CYLINDRICAL INSTRUMENT SHANK

(71) Applicant: DENTSPLY SIRONA inc., York, PA (US)

(72) Inventors: Metin Ertugrul, Rodermark (DE); Siegfried Goisser, Einhausen (DE); Stefan Gobel, Langen (DE)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 15/566,226

(22) PCT Filed: Apr. 18, 2016

(86) PCT No.: PCT/EP2016/058523
§ 371 (c)(1),
(2) Date: Oct. 13, 2017

(87) PCT Pub. No.: WO2016/166367
PCT Pub. Date: Oct. 20, 2016

(65) Prior Publication Data
US 2018/0132971 A1     May 17, 2018

(30) Foreign Application Priority Data
Apr. 16, 2015   (DE) .................. 10 2015 206 904

(51) Int. Cl.
*A61C 1/14*     (2006.01)
*A61B 17/16*    (2006.01)
(Continued)

(52) U.S. Cl.
CPC ............ *A61C 1/144* (2013.01); *A61B 17/162* (2013.01); *B23B 31/1177* (2013.01); *B23B 31/201* (2013.01)

(58) Field of Classification Search
CPC ... A61C 1/144; A61B 17/162; B23B 31/1177; B23B 31/201; B23B 31/20;
(Continued)

(56) References Cited

U.S. PATENT DOCUMENTS 2,996,301 A * 8/1961 Cox .................... B23B 31/4033
                                                            279/2.02
4,573,918 A   3/1986 Bareth
(Continued)

FOREIGN PATENT DOCUMENTS

DE      3346248 A1    7/1985
EP      0273259 A1    7/1988
(Continued)

OTHER PUBLICATIONS

International Search Report and Written Opinion for PCT/EP2016/058523 dated Aug. 18, 2016.
(Continued)

*Primary Examiner* — Sean M Michalski
*Assistant Examiner* — Mirayda A Aponte
(74) *Attorney, Agent, or Firm* — Dentsply Sirona Inc.

(57) ABSTRACT

The invention relates to a clamping device for clamping a cylindrical instrument shank, in particular, a dental instrument, the clamping device including a spring-loaded element for holding the instrument shank, a hollow shaft for transmitting a rotational movement, and a plunger, with the spring-loaded element being designed as a sleeve with a cylindrical wall, a first opening and a second opening; and the wall having cut-outs. The spring-loaded element, the shaft and the plunger have axes of rotation that are arranged coaxially; the shaft protrudes at least partially into the first opening of the spring-loaded element; and the plunger protrudes at least partially into the second opening of the spring-loaded element.

10 Claims, 2 Drawing Sheets

(51) Int. Cl.
*B23B 31/117* (2006.01)
*B23B 31/20* (2006.01)

(58) Field of Classification Search
CPC ....... B23B 2231/2091; Y10T 279/1045; Y10T 279/17435; Y10T 279/17307; Y10T 279/17521
USPC ........................................................ 433/127
See application file for complete search history.

(56) References Cited

U.S. PATENT DOCUMENTS

| | | | | |
|---|---|---|---|---|
| 5,542,685 | A * | 8/1996 | Allen | B23B 31/4073 |
| | | | | 279/141 |
| 6,065,966 | A * | 5/2000 | Lohn | A61B 17/162 |
| | | | | 433/128 |
| 7,303,394 | B2 * | 12/2007 | Ma tre | A61B 17/162 |
| | | | | 433/127 |
| 2004/0014005 | A1 * | 1/2004 | Kuhn | A61B 17/162 |
| | | | | 433/127 |
| 2008/0167652 | A1 * | 7/2008 | Reinhard | A61B 17/162 |
| | | | | 606/80 |

FOREIGN PATENT DOCUMENTS

| | | | | |
|---|---|---|---|---|
| EP | 1709930 | A1 | 10/2006 | |
| EP | 2196274 | A1 * | 6/2010 | ........... B23B 31/201 |
| EP | 2196274 | A1 | 6/2010 | |

OTHER PUBLICATIONS

International Preliminary Report on Patentability for PCT/EP2016/058523 dated Oct. 17, 2017.

* cited by examiner

CLAMPING DEVICE FOR CLAMPING A CYLINDRICAL INSTRUMENT SHANK

TECHNICAL FIELD

The invention relates to a clamping device that is intended for clamping a cylindrical instrument shank, in particular, a dental instrument, and that comprises a spring-loaded element for holding the instrument shank, a hollow shaft for transmitting a rotational movement, and a plunger, wherein the spring-loaded element is designed as a sleeve with a cylindrical wall, a first opening and a second opening; and the wall has cut-outs.

PRIOR ART

Various variants of clamping devices for clamping a cylindrical instrument shank, which is to be driven in rotation, are known from the prior art.

The clamping device, described in the published document EP 0 273 259 A1, comprises a clamping sleeve with tongues, which are formed by longitudinal slots and which hold the instrument shank. Contact surfaces or, more specifically, holding surfaces are formed, in particular, at the edges.

Therefore, it is also known or rather it is also customary to make these areas, which are subject to very high stress, of a corrosion resistant, hard material or to coat such areas with such a material.

The published document DE 33 46 248 A1 discloses, for example, a clamping device for clamping a dental instrument with a two-part clamping device. The clamping force is provided by a spring-loaded element and is transmitted through the structurally separate clamping jaws to the instrument shank to be held. This feature makes it possible, on the one hand, to produce the surfaces, which are in contact with the instrument shank, of a corrosion-resistant material that is as hard as possible and, on the other hand, makes the maintenance easier, because only the clamping jaws have to be replaced if the contact surfaces show any wear.

The drawback with the clamping devices described above is the relatively small dimensions of the holding surfaces or, more specifically, edges and the resulting very high force inputs.

Therefore, the object of the present invention is to provide a particularly resilient clamping device.

SUMMARY

This engineering object is achieved by means of a clamping device that is intended for clamping a cylindrical instrument shank, in particular, a dental instrument, and that comprises a spring-loaded element for holding the instrument shank, a hollow shaft for transmitting a rotational movement, and a plunger. The spring-loaded element is designed as a sleeve with a cylindrical wall, a first opening and a second opening, where in this case the wall has cut-outs. The spring-loaded element, the shaft and the plunger have axes of rotation that are arranged coaxially, where in this case the shaft protrudes at least partially into the first opening of the spring-loaded element; and the plunger protrudes at least partially into the second opening of the spring-loaded element.

The torque, which is transmitted to the shaft by means of, for example, an outer shaft, can be transmitted directly and/or by means of the spring-loaded element and/or the plunger to an instrument shank that is held in the spring-loaded element. The instrument shank is held in the spring-loaded element in a non-positive engaging and/or positive engaging manner. In this case a non-positive engagement is achieved by means of a radial spring force of the spring-loaded element. A positive engagement may be achieved, for example, by means of a groove on the spring-loaded element and a correspondingly shaped projection, such as, for example, a pin or cone, on the instrument shank or in some other known manner.

The spring-loaded element of the invention represents, without additional intermediate parts, the contact partner of the instrument and, as a result, makes feasible a small and compact design of the clamping device.

Since a component, i.e., consisting of the shaft and the plunger, engages with the spring-loaded element on both sides, the actuating force for opening or, more specifically, widening the spring-loaded element is used twice and may be correspondingly less.

The sleeve-shaped design of the spring-loaded element also provides an elastically springy area that is as long as possible and a radially acting contact force. In this way the objective of less wear and a good concentricity is achieved. Since the clamp travel in clamping position is significantly greater than the tolerance variations in the diameters of the clamped instrument shank, the net result is, furthermore, just small variations in the holding forces and a large tolerance to deviations of the diameter of the instrument shank.

The cut-outs in the wall of the spring-loaded element offer the possibility of optimizing the use of the materials in order to keep the maximum stress as low as possible and, in so doing, to ensure a large number of possible instrument changes. In order to fulfill this objective, it is possible to optimize, in particular, the special design in terms of the width, length and number of the cut-outs. For example, a loop-like shape that makes oblong elastic holding surfaces feasible can be achieved by means of slots that are staggered on both sides. However, the wider such slots are formed, the more the holding surfaces degenerate into lines.

The spring-loaded element may also comprise circular cut-outs, such as, for example, bores that are distributed, for example, uniformly over the entire shell of the spring-loaded element. Another variant is a base body, which is weakened by diamond meshes, i.e., a spring-loaded element having a shell with diamond cut-outs arranged in rows and columns.

The small number of components of the clamping device and the simplicity of these components permit a particularly cost-effective production.

Advantageously, the spring-loaded element is connected to the shaft in a positive engaging and/or non-positive engaging manner. This aspect allows the rotational movement to be transmitted directly from the shaft to the spring-loaded element. A positive engagement can be achieved, for example, by means of a projection on the shaft and a corresponding cut-out in the wall of the spring-loaded element or by means of a projection, for example a pin, on the spring-loaded element and a corresponding cut-out, for example, a groove, on the shaft.

Advantageously, the cut-outs are formed in the wall of the spring-loaded element as slots, extending at least approximately parallel to the axis of rotation of the spring-loaded element, where in this case at least one slot begins at the first opening of the spring-loaded element, and at least a second slot begins at the second opening, in order to provide a radial spring force that acts possibly over the entire height of the spring-loaded element. An even number of slots, for example, four or six slots is advantageous for a simple production.

Advantageously the slots, beginning at the first opening, are arranged in the circumferential direction of the spring-loaded element in such a way that they are offset from the slots, beginning at the second opening. This feature meets the objective of achieving a loop-like shape of the spring-loaded element that makes a long, elastically springy area feasible even in a small design space.

Advantageously the slots have a wider cut-out on an end facing away from the opening of the spring-loaded element, with the result that the elasticity of the spring-loaded element is increased.

Advantageously the spring-loaded element is made of an acid and corrosion resistant material. This aspect makes it possible to extend the service life of the spring-loaded element, which is particularly susceptible to wear in its capacity as the direct contact partner of the instrument. It goes without saying that in order to extend the service life, instead of forming the whole spring-loaded element from an acid and corrosion resistant material, it is possible to coat the inner surfaces, i.e., those surfaces which make contact with the instrument and are subject to wear, with such a material.

Advantageously, the spring-loaded element has actuating surfaces, which slope obliquely downwards towards the inside, around the first and second openings, in order to allow the plunger and the shaft to move easily into the spring-loaded element.

Furthermore, the invention relates to a dental preparation instrument that comprises a clamping device of the kind described above.

BRIEF DESCRIPTION OF THE DRAWINGS

Exemplary embodiments of the invention are shown in the drawings. The drawings show in FIG. 1 in schematic form a representation of a clamping device according to the invention.

DETAILED DESCRIPTION

Figure 1:
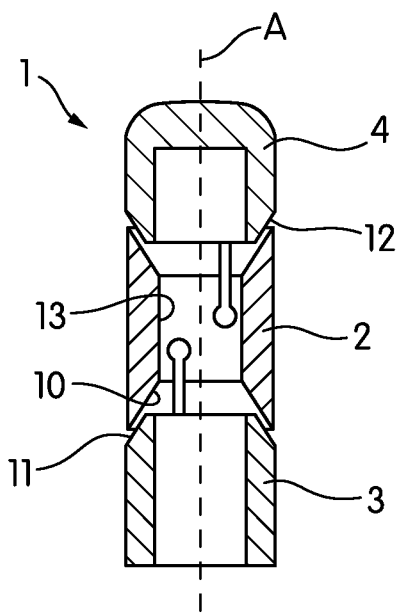

FIG. 1 shows an inventive clamping device 1, which comprises a spring-loaded element 2, a shaft 3 and a plunger 4. The spring-loaded element 2, the shaft 3 and the plunger 4 each have an axis of rotation and are arranged coaxially with respect to this axis A.

Figure 2A:
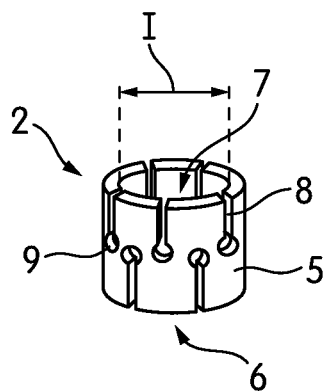
FIGS. 2A, B a first embodiment and a second embodiment of a spring-loaded element according to the invention.

The spring-loaded element 2, which is shown in isolation in FIG. 2A, is formed as a sleeve comprising a cylindrical wall 5, a first opening 6 and a second opening 7 and has an inside diameter I, which is slightly smaller than a diameter of an instrument shank that is to be clamped.

In the embodiment shown in FIG. 2A, a radial widening of the spring-loaded element 2 or, more specifically, a radially acting spring force is possible due to the slot-shaped cut-outs 8, which are staggered on both sides and which extend from the two openings 6, 7 of the sleeve-shaped spring-loaded element 2 in the direction of the respective opposite opening 6, 7. In the exemplary embodiment that is shown, the slot-shaped cut-outs 8 terminate in wider circular cut-outs 9.

Figure 2B:
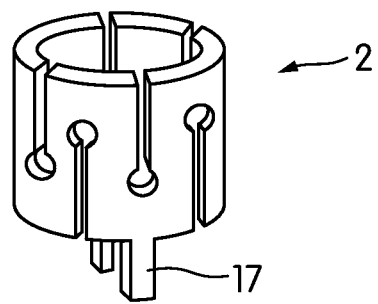

For reasons relating to production, an even number of slots on each side is to be preferred, as shown, for example, in FIG. 2B.

Furthermore, the spring-loaded element 2 has, according to the embodiment shown in FIG. 1, actuating surfaces 10 that slope obliquely downwards towards the inside. The shaft 3 and the plunger 4 have corresponding actuating surfaces 11, 12 that slope obliquely downwards towards the outside, so that the partial insertion of the shaft 3 and plunger 4 into one end of the spring-loaded element 2 is made easier. The obliquely downwards sloping actuating surfaces 10, 11, 12 may be designed, for example, in a cone shape or truncated pyramid shape.

Moving the shaft 3 and/or the plunger 4 into the spring-loaded element 2 causes said spring-loaded element to widen or rather to open due to an axially generated actuating force. In this case the movement of the inner surface 13 of the spring-loaded element 2, where said inner surface is used as the surfaces that make contact with the instrument shank or, more specifically, as the holding surfaces for the instrument shank, is carried out strictly in the radial direction as a result of the inventive coaxial arrangement of the sleeve-shaped and interlocking components. The inner surface 13 stays largely parallel to the axis of rotation A of the clamping device 1. This feature allows an inner surface 13, which is used as the contact surfaces or rather the holding surfaces, to be applied uniformly, even in the case of instrument shank diameters that vary widely.

If the shaft 3 and the plunger 4 are moved out of the spring-loaded element 2 again, then this spring-loaded element contracts in the radial direction and holds an inserted instrument shank along the entire inner surface 13. This aspect achieves the objective of a pressure per unit of area that is as low as possible; and, as a result, the wear is reduced.

Figure 3A:
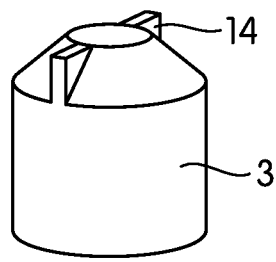
FIGS. 3A, B a first embodiment and a second embodiment of a clamping device according to the invention.

In order to allow the rotational movement to be transmitted from the shaft 3 to an instrument, the shaft 3 may comprise, as shown in FIG. 3A, a projection 14 for a positive engaging connection with the instrument-holding spring-loaded element 2 or, more specifically, a corresponding cut-out of the spring-loaded element 2.

Figure 3B:
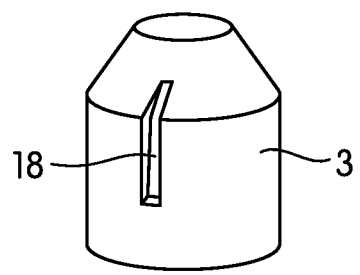

It is also just as possible to provide a positive engaging connection between the spring-loaded element 2 and the shaft 3 by means of one or more projections 17, arranged on the spring-loaded element 2, and one or more corresponding cut-outs 18 on the shaft 3, as shown in FIGS. 2B and 3B.

Even a strictly non-positive engaging connection between the shaft and the spring-loaded element or a non-positive and/or positive engaging connection between the spring-loaded element and an additional component, which transmits the rotational movement, is possible.

Figure 4:
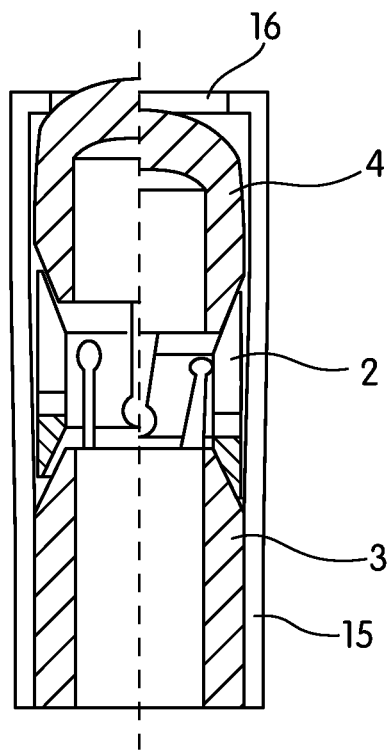
FIG. 4 in schematic form a representation of an additional embodiment of the clamping device.

The clamping device 1 may also comprise, as shown in the embodiment in FIG. 4, additionally an outer shaft 15, which transmits a torque to the shaft 3 or to the shaft 3 and the spring-loaded element 2, for which purpose the components are connected to each other in a non-positive engaging and/or positive engaging manner. According to the embodiment shown in FIG. 4, the outer shaft 15 envelops the shaft 3, the plunger 4 and the spring-loaded element 2 and has an opening 16 and/or an actuating element for actuating the plunger 4 in a manner known from the prior art.

Figure 5:
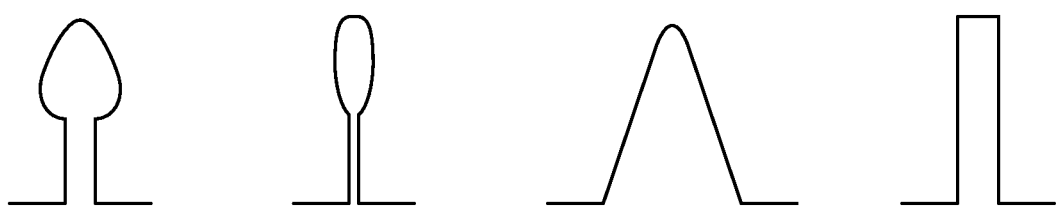
FIG. 5 various embodiments of the cut-outs in the wall of the spring-loaded element.

The cut-outs 8 for weakening the wall 5 of the spring-loaded element 2 may have a wide range of shapes. Some examples are shown in FIG. 5.

LIST OF REFERENCE NUMERALS AND CHARACTERS 1 clamping device
2 spring-loaded element 3 shaft
4 plunger
5 wall of the spring-loaded element
6 first opening of the spring-loaded element
7 second opening of the spring-loaded element
8 cut-outs
9 cut-outs
10 actuating surface of the spring-loaded element
11 actuating surface of the shaft
12 actuating surface of the plunger
13 inner surface of the spring-loaded element
14 projection
15 outer shaft
16 opening
17 projection
18 cut-out
A axis of rotation of the clamping device
I inside diameter

The invention claimed is:

1. A clamping device for clamping a cylindrical instrument shank, said clamping device comprising:
   a spring-loaded element for holding the instrument shank,
   a hollow shaft disposed on one end of the spring-loaded element for transmitting a rotational movement,
   a plunger disposed on another end of the spring loaded element, and
   an outer shaft that envelopes the hollow shaft, the plunger and the spring-loaded element, said outer shaft transmitting a torque to the hollow shaft or to the spring-loaded element,
   wherein the spring-loaded element is designed as a sleeve with a cylindrical wall, a first opening and a second opening; and the wall has cut-outs, wherein the spring-loaded element, the hollow shaft and the plunger have axes of rotation that are arranged coaxially; the hollow shaft protrudes at least partially into the first opening of the spring-loaded element; and the plunger protrudes at least partially into the second opening of the spring-loaded element,
   wherein the cut-outs are formed in the wall of the spring-loaded element as a plurality of slots, extending at least approximately parallel to the axis of rotation of the spring-loaded element,
   wherein said slots are configured to provide a radial spring force that acts over a height of the spring-loaded element by at least one slot of the plurality of slots being formed at the first opening of the spring-loaded element, and at least another slot of the plurality of slots being formed at the second opening, and the at least one slot formed at the first opening being constructed to be offset from the at least another slot formed at the second opening and
   wherein the spring-loaded element holds the instrument shank in a first non-positive engaging manner in which inner surfaces of the spring-loaded element are configured to be approximately parallel to said axis of rotation of the spring-loaded element and to make contact with the instrument shank along the height of the spring-loaded element in order to exert said radial spring force on the instrument shank along said height of the spring-loaded element such that the rotational movement is transferred from the spring-loaded element to the instrument shank.

2. The clamping device as claimed in claim 1, wherein the slots beginning at the first opening are arranged in the circumferential direction of the spring-loaded element in such a way that they are offset from the slots, beginning at the second opening.

3. The clamping device as claimed in claim 1, wherein the slots have a wider cut-out on an end facing away from the opening of the spring-loaded element.

4. The clamping device as claimed in claim 1, wherein the spring-loaded element is made of an acid and corrosion resistant material.

5. The clamping device as claimed in claim 1, wherein the spring-loaded element has actuating surfaces, which slope obliquely downwards towards the inside, around the first and the second opening, said actuating surfaces being configured such that moving the hollow shaft or the plunger into the spring-loaded element causes said spring-loaded element to widen due to an axially generated actuating force.

6. The clamping device as claimed in claim 1, wherein the clamping device is capable of being arranged in a dental preparation instrument.

7. The clamping device as claimed in claim 1, wherein in addition to providing said radial spring force, one or more of the plurality of slots on said one end of the spring-loaded element are configured to engage the hollow shaft in a first positive engaging manner and one or more of the plurality of slots on said another end of the spring-loaded element are configured to engage the plunger in a second positive engaging manner.

8. The clamping device as claimed in claim 1, wherein the hollow shaft is configured to engage the spring-loaded element in both (i) a first positive engaging manner, through the engagement of one or more projections on the hollow shaft or on the spring-loaded element with one or more slots on the hollow shaft or on the spring loaded element and (ii) a second non-positive engaging manner.

9. The clamping device as claimed in claim 8, wherein the hollow shaft, outer shaft and spring-loaded element are connected to each other in both a third positive engaging manner and a third non-positive engaging manner.

10. The clamping device as claimed in claim 1, wherein the instrument shank is held in the spring-loaded element in both a second positive engaging manner and the first non-positive engaging manner.

* * * * *